United States Patent
Budde et al.

(10) Patent No.: US 11,426,334 B2
(45) Date of Patent: *Aug. 30, 2022

(54) SURFACE-REACTED CALCIUM CARBONATE FOR MODIFYING THE BIOMECHANICAL PROPERTIES OF THE SKIN

(71) Applicant: OMYA INTERNATIONAL AG, Oftringen (CH)

(72) Inventors: Tanja Budde, Brittnau (CH); Anaïs Hecker, Oftringen (CH)

(73) Assignee: OMYA INTERNATIONAL AG, Oftringen (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/961,671

(22) PCT Filed: Jan. 23, 2019

(86) PCT No.: PCT/EP2019/051656
§ 371 (c)(1),
(2) Date: Jul. 11, 2020

(87) PCT Pub. No.: WO2019/145372
PCT Pub. Date: Aug. 1, 2019

(65) Prior Publication Data
US 2020/0397672 A1    Dec. 24, 2020

(30) Foreign Application Priority Data

Jan. 26, 2018 (EP) .................................. 18153689

(51) Int. Cl.
| | | |
|---|---|---|
| A61K 8/19 | (2006.01) | |
| A61K 8/02 | (2006.01) | |
| A61Q 1/04 | (2006.01) | |
| A61Q 1/10 | (2006.01) | |
| A61Q 17/04 | (2006.01) | |
| A61Q 19/08 | (2006.01) | |

(52) U.S. Cl.
CPC .............. *A61K 8/19* (2013.01); *A61K 8/0241* (2013.01); *A61Q 1/04* (2013.01); *A61Q 1/10* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,004,584 | A | 12/1999 | Peterson et al. |
| 6,165,510 | A | 12/2000 | Baines et al. |
| 6,461,626 | B1 | 10/2002 | Rabe et al. |
| 9,144,434 | B1 | 9/2015 | Rodan et al. |
| 9,593,244 | B2 | 3/2017 | Gane et al. |
| 2004/0020410 | A1 | 2/2004 | Gane et al. |
| 2015/0218381 | A1 | 8/2015 | O'Halloran et al. |
| 2015/0290094 | A1* | 10/2015 | Izumikawa ............. C01F 11/18 424/401 |
| 2016/0271025 | A1* | 9/2016 | Budde ...................... A61K 8/19 |

FOREIGN PATENT DOCUMENTS

| | | |
|---|---|---|
| EP | 0173391 A2 | 3/1986 |
| EP | 1712523 A1 | 10/2006 |
| EP | 1712597 A1 | 10/2006 |
| EP | 2168572 A1 | 3/2010 |
| EP | 2264108 A1 | 12/2010 |
| EP | 2264109 A1 | 12/2010 |
| EP | 2371766 A1 | 10/2011 |
| EP | 2447213 A1 | 5/2012 |
| EP | 2524898 A1 | 11/2012 |
| EP | 2883573 A1 | 6/2015 |
| EP | 2910237 A1 | 8/2015 |
| EP | 3045503 A1 | 7/2016 |
| EP | 2245095 B1 | 2/2017 |
| KR | 20030062371 | 7/2003 |
| WO | 00/39222 A1 | 7/2000 |
| WO | 2004/083316 A1 | 9/2004 |
| WO | 2005/121257 A2 | 12/2005 |
| WO | 2009/074492 A1 | 6/2009 |
| WO | 2013/142473 A1 | 9/2013 |

OTHER PUBLICATIONS

International Search Report from PCT/EP2019/051651, dated Mar. 11, 2019, 4 pages.
Written Opinion from PCT/EP2019/051651, dated Mar. 11, 2019, 7 pages.
International Search Report from PCT/EP2019/051656, dated Mar. 15, 2019, 3 pages.
Written Opinion from PCT/EP2019/051656, dated Mar. 15, 2019, 6 pages.
Gane et al. (1996) "Void Space Structure of Compressible Polymer Spheres and Consolidated Calcium Carbonate Paper-Coating Formulations" Ind. Eng. Chem. Res., vol. 35, pp. 1753-1764.
Regulation (EC) No 1223/2009 of the European Parliament and of the Council of Nov. 30, 2009 on Cosmetic Products (151 pages).
U.S. Appl. No. 16/961,312 nonfinal Office action dated May 27, 2021, 2021, 21 pages.
U.S. Appl. No. 16/961,312 Response to nonfinal Office action dated Aug. 22, 2021, 13 pages.
U.S. Appl. No. 16/961,312 final Office action dated Aug. 31, 2021, 2021, 24 pages.
U.S. Appl. No. 16/961,312 Response to final Office action dated Nov. 30, 2021, 13 pages.
U.S. Appl. No. 16/961,312 nonfinal Office action dated Mar. 16, 2022, 11 pages.
U.S. Appl. No. 16/961,312 Response to nonfinal Office action dated May 29, 2022, 8 pages.

(Continued)

Primary Examiner — Melissa L Fisher
(74) Attorney, Agent, or Firm — ALGM LLP; Harry J. Guttman

(57) ABSTRACT

The present invention refers to the use of a surface-reacted calcium carbonate in a cosmetic and/or skin care composition as an agent for modifying the biomechanical properties of the skin.

21 Claims, 1 Drawing Sheet

(56) References Cited

OTHER PUBLICATIONS

KR20030062371 (Jul. 25, 2003), English language translation of publication, 6 pages.
Deckner (2014) "Finding Alternatives to Synthetic Exfoliating Beads" posted at www.Knowledge.ULProspector.com, last accessed Nov. 17, 2016. (3 pages).

* cited by examiner

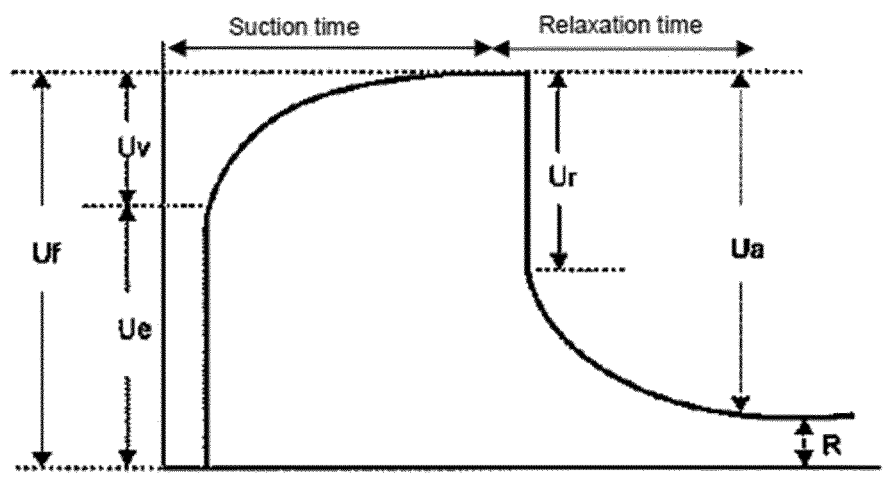
- Uf: *final deformation (firmness)*
- Ue: *immediate extensibility*
- Uv: *delayed distension (plasticity / viscoelasticity)*
- Ur: *immediate retraction (tonicity)*
- Ua: *total recovery of the initial state*
- R: *residual deformation at the end of measuring cycle*

SURFACE-REACTED CALCIUM CARBONATE FOR MODIFYING THE BIOMECHANICAL PROPERTIES OF THE SKIN

CROSS-REFERENCE TO RELATED APPLICATIONS

This application is a National Stage Entry of International Application No. PCT/EP2019/051656 filed Jan. 23, 2019, entitled "SURFACE-REACTED CALCIUM CARBONATE FOR MODIFYING THE BIOMECHANICAL PROPERTIES OF THE SKIN", and which claims priority to EP Application No 18153689.7 filed Jan. 26, 2018 entitled "SURFACE-REACTED CALCIUM CARBONATE FOR MODIFYING THE BIOMECHANICAL PROPERTIES OF THE SKIN."

The present invention refers to the use of a surface-reacted calcium carbonate in a cosmetic and/or skin care composition as an agent for modifying the biomechanical properties of the skin.

The biological composition and the cellular physiology of the skin changes over the lifespan of a human being. Several factors contribute to the change in composition and cellular activity. For example, it is known that epidermal turnover rate slows down with increasing age of an individual. Furthermore, aged skin, or skin which has been excessively exposed to UV radiation, shows a loss and/or reduced biosynthesis of certain collagen types and elastin, which weakens the structure and integrity of the extracellular matrix of the skin. Malfunction and/or loss of glycosaminoglycans and/or hyaluronic acid in the dermis and epidermis can further lead to a decreased retention of moisture in these skin layers. The result of these physiological and biological changes is an alteration of the skin appearance, what is often referred to as "old" or "aged" skin. For example, the skin gradually loses its elasticity, shows an increased plasticity, i.e. a tendency to maintain a certain shape after deformation, forms wrinkles and/or shows an altered pigmentation.

The appearance of elastic and firm skin with an even pigmentation and without wrinkles, or stated differently, the appearance of young skin, is usually considered by the surrounding as being more attractive or pleasant than that of aged skin. Thus, many individuals seek to stop, or at least slow down, the process of skin ageing, or at least certain aspects of the ageing process.

In view of the foregoing, there is a constant need for agents for the use in cosmetic and/or skin care compositions, which help to restore the biomechanical properties of the skin, especially of the facial skin. There is also a need for agents for the use in cosmetic and/or skin care compositions, which stop, or at least slow down, the alteration of the biomechanical properties of the skin, especially of the facial skin.

Accordingly, an objective of the present invention may be seen in the provision of an agent for the use in a cosmetic and/or skin care composition, which modifies the biomechanical properties of the skin, and especially of the facial skin. Another objective of the present application is the provision of an agent for the use in a cosmetic and/or skin care composition, which increases the skin firmness and provides reduced skin irritations. A further objective of the present application is the provision of an agent for the use in a cosmetic and/or skin care composition, which additionally increases skin elasticity and decreases the skin plasticity.

One or more of the foregoing objectives is/are solved by the present invention.

According to one aspect of the present invention, the use of a surface-reacted calcium carbonate in a cosmetic and/or skin care composition as an agent for modifying the biomechanical properties of the skin is provided. The surface-reacted calcium carbonate has a volume median particle size $d_{50}$ from 0.1 to 90 μm, and is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

Advantageous embodiments of the inventive use are defined in the corresponding sub-claims.

According to one embodiment of the present invention, the surface-reacted calcium carbonate has a volume median particle size $d_{50}$ from 0.5 to 50 μm, preferably from 1 to 40 μm, more preferably from 1.2 to 30 μm, and most preferably from 1.5 to 15 nm.

According to one embodiment of the present invention, the surface-reacted calcium carbonate has a specific surface area of from 15 m²/g to 200 m²/g, preferably from 20 m²/g to 180 m²/g, and more preferably from 25 m²/g to 160 m²/g, measured using nitrogen and the BET method.

According to one embodiment of the present invention, the natural ground calcium carbonate is selected from the group consisting of marble, chalk, limestone, and mixtures thereof, or the precipitated calcium carbonate is selected from the group consisting of precipitated calcium carbonates having an aragonitic, vateritic or calcitic crystal form, and mixtures thereof.

According to one embodiment of the present invention, the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

According to one embodiment of the present invention, the modification of the biomechanical properties of the skin refers to the skin firmness, preferably to an increased skin firmness.

According to one embodiment of the present invention, the skin refers to the skin of the arms, especially the hands, the skin of the legs, especially the feet, the skin of the neck, the skin of the chest, and/or the skin of the face, preferably the skin of the face. According to another embodiment of the present invention, the cosmetic and/or skin care composition has a pH value of ≤8.5, preferably ≤8.0, more preferably preferably ≤7.5, even more preferably ≤7.0, and most preferably from 4.0 to 7.0. According to one embodiment of the present invention, the surface-reacted calcium carbonate is present in the cosmetic and/or skin care composition in an amount from 0.1 to 50 wt.-%, based on the total weight of the composition, preferably from 0.5 to 20 wt.-%, more preferably from 1 to 10 wt.-%, and most preferably from 3 to 10 wt.-%.

According to one embodiment of the present invention, wherein the cosmetic and/or skin care composition further comprises water and/or at least one oil, preferably the at least one oil is selected from the group consisting of vegetable oils and esters thereof, alkanecoconutester, plant extracts, animal fats, siloxanes, silicones, fatty acids and esters thereof, petrolatum, glycerides and pegylated derivatives thereof, and mixtures thereof.

According to one embodiment of the present invention, the cosmetic and/or skin care composition comprises at least one active agent being adsorbed onto and/or absorbed into the surface of the surface-reacted calcium carbonate.

According to one embodiment of the present invention, the at least one active agent is selected from pharmaceutically active agents, biologically active agents, vitamins, disinfecting agents, preservatives, flavouring agents, surfactants, oils, fragrances, essential oils, and mixtures thereof.

According to one embodiment of the present invention, the composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

According to one embodiment of the present invention, the cosmetic and/or skin care composition is selected from an eye make-up product, a facial make-up product, a lip care product, a hand care product, a skin care product, or a combination product thereof.

According to one embodiment of the present invention, the surface-reacted calcium carbonate does not lead to negative side-effects, and preferably does not lead to skin irritation, after application on the skin.

It should be understood that for the purposes of the present invention, the following terms have the following meanings:

A "cosmetic and/or skin care" composition in the meaning of the present invention refers to a composition that is applied onto the skin. That is to say, a "cosmetic and/or skin care" composition does not encompass a composition that is typically taken up orally.

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon treatment with an $H_3O^+$ ion donor (e.g., by use of water-soluble free acids and/or acidic salts) in aqueous environment followed by a crystallization process which may occur in the absence or presence of further crystallization additives.

An "$H_3O^+$ ion donor" in the context of the present invention is a Brønsted acid and/or an acid salt, i.e. a salt containing an acidic hydrogen.

The term "acid" as used herein refers to an acid in the meaning of the definition by Brønsted and Lowry (e.g., $H_2SO_4$, $HSO_4^-$).

The term "free acid" refers only to those acids being in the fully protonated form (e.g., $H_2SO_4$).

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are smaller than this particle size. For the purpose of the present invention, the particle size is specified as weight median particle size $d_{50}$(wt.) unless indicated otherwise. Particle sizes were determined by using a Sedigraph™ 5100 instrument or Sedigraph™ 5120 instrument of Micromeritics Instrument Corporation. The method and the instrument are known to the skilled person and are commonly used to determine the particle size of fillers and pigments. The measurements were carried out in an aqueous solution of 0.1 wt.-% $Na_4P_2O_7$.

The "particle size" of surface-reacted calcium carbonate herein is described as volume-based particle size distribution. Volume median particle size $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The term "particulate" in the meaning of the present application refers to materials composed of a plurality of particles. Said plurality of particles may be defined, for example, by its particle size distribution. The expression "particulate material" may comprise granules, powders, grains, tablets, or crumbles.

The "specific surface area" (expressed in $m^2/g$) of a material as used throughout the present document can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 100° C. under vacuum for a period of 30 min prior to measurement. The total surface area (in $m^2$) of said material can be obtained by multiplication of the specific surface area (in $m^2/g$) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

The "modification of biomechanical properties of the skin" refers to the modification of, for example, skin firmness, skin elasticity, or skin plasticity. The expression is not meant to encompass a skin appearance modification by covering and/or mattifying the surface of the skin.

The expression "skin firmness" in the meaning of the present application refers to the natural tension of the skin.

An increased skin firmness is usually associated with skin showing less signs of ageing, and thus is usually associated with young skin. In this context, it is to be understood that an "increased skin firmness" refers to "a decreased skin firmness parameter", i.e. skin firmness parameter (R0 (Uf)). The decrease of the skin firmness parameter is associated with skin showing less signs of ageing. The "skin firmness parameter", and thus the "skin firmness", can be measured, for example, by a suction method, wherein a device creates a vacuum, e.g. 450 mbar, on a certain area of the skin, typically with a diameter of 2 to 8 mm, preferably 2 mm. The applied vacuum sucks the skin into the device. After breaking the vacuum, the skin tries to restore its original state/shape. Suction and relaxation times may be 3 seconds. An optical probe in the device measures the penetration depth of the skin into the device, i.e. its final deformation. Based thereon, the total and/or relative values of skin firmness can be determined. A suitable device for measuring the skin firmness is, for example, a MPA 580 Cutometer® from Courage & Khazaka.

The expression "skin elasticity" in the meaning of the present application refers to the skin's capacity to return to its initial state after being stretched. An increased skin elasticity is usually associated with skin showing less signs of ageing, and thus an elastic skin is usually associated with young skin. "Skin elasticity" may be measured, for example, by a suction method, wherein a device creates a vacuum, e.g. 450 mbar, on a certain area of the skin, typically with a diameter of 2 to 8 mm, preferably 2 mm. The applied vacuum sucks the skin into the device. After breaking the vacuum, the skin tries to restore its original state/shape. Suction and relaxation times may be 3 seconds. An optical probe in the device measures parameters of final deformation, immediate extensibility, delayed distension, immediate retraction and/or total recovery of the initial state. Based thereon, the total and/or relative values of skin elasticity can be determined such as biological skin elasticity, net skin elasticity or raw skin elasticity. An increase of one or more of these values can be interpreted as increase in overall skin elasticity. A suitable device for measuring the skin elasticity is, for example, a MPA 580 Cutometer® from Courage & Khazaka.

The expression "skin plasticity" in the meaning of the present application refers to the skin's capacity to maintain a certain shape after its deformation. A decreased skin plasticity is usually associated with skin showing less signs of ageing. "Skin plasticity" may be measured, for example, by a suction method, wherein a device creates a vacuum, e.g. 450 mbar, on a certain area of the skin, typically with a diameter of 2 to 8 mm, preferably 2 mm. The applied vacuum sucks the skin into the device. After breaking the vacuum, the skin tries to restore its original state/shape. Suction and relaxation times may be 3 seconds. An optical probe in the device measures parameters of final deformation, immediate extensibility, delayed distension, immediate retraction and/or total recovery of the initial state. Based thereon, the total and/or relative values of skin plasticity can be determined. A suitable device for measuring the skin plasticity is, for example, a MPA 580 Cutometer® from Courage & Khazaka.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt.-%, preferably less than or equal to 0.5 wt.-%, more preferably less than or equal to 0.2 wt.-%, and most preferably between 0.03 and 0.07 wt.-%, based on the total weight of the dried material.

For the purpose of the present application, "water-insoluble" materials are defined as those which, when mixed with 100 ml of deionised water and filtered at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of solid material following evaporation at 95 to 100° C. of 100 g of said liquid filtrate. In order to assess whether a material is an insoluble or soluble material in the meaning of the present invention, the sample size is greater than 0.1 g, preferably 0.5 g or more.

A "suspension" or "slurry" in the meaning of the present invention comprises undissolved solids and water, and optionally further additives, and usually contains large amounts of solids and, thus, is more viscous and can be of higher density than the liquid from which it is formed.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

In the following preferred embodiments of the inventive composition will be set out in more detail.

Surface-Reacted Calcium Carbonate

The present invention refers to the use of a surface-reacted calcium carbonate in a cosmetic and/or skin care composition as an agent for modifying the biomechanical properties of the skin, wherein the surface-reacted calcium carbonate has a volume median particle size $d_{50}$ from 0.1 to 90 μm, and wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

In a preferred embodiment of the invention the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$) and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground calcium carbonate or precipitated calcium carbonate is in form of particles having a weight median particle size $d_{50}$ of 0.05 to 10.0 µm, preferably 0.2 to 5.0 µm, and most preferably 0.4 to 3.0 µm. According to a further embodiment of the present invention, the natural ground calcium carbonate or precipitated calcium carbonate is in form of particles having a weight top cut particle size $d_{98}$ of 0.15 to 30 µm, preferably 0.6 to 15 µm, more preferably 1.2 to 10 µm, most preferably 1.5 to 4 µm, especially 1.6 µm.

The natural ground calcium carbonate and/or precipitated calcium carbonate may be used dry or suspended in water. Preferably, a corresponding slurry has a content of natural ground calcium carbonate or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural ground calcium carbonate or precipitated calcium carbonate is treated with carbon dioxide. If a strong acid such as sulphuric acid or hydrochloric acid is used for the $H_3O^+$ ion donor treatment of the natural ground calcium carbonate or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, typically from about 5 to about 30 min. Alternatively, the at least one $H_3O^+$ ion donor is added over a time period of about 30 min, preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

It is appreciated that the $H_3O^+$ ion donor treatment and treatment with carbon dioxide can be carried over a wide temperature range. Preferably, the $H_3O^+$ ion donor treatment and treatment with carbon dioxide can be carried out at room temperature or elevated temperature. For example, if the $H_3O^+$ ion donor treatment and treatment with carbon dioxide is carried out at elevated temperature, the treatment is preferably in a range from 30 to 90° C., more preferably from 40 to 80° C. and most preferably from 50 to 80° C., such as from 60 to 80° C.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground calcium carbonate or precipitated calcium carbonate, the natural ground calcium carbonate or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural ground calcium carbonate or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural ground calcium carbonate or precipitated calcium carbonate in the form of granules or a powder.

The surface-reacted calcium carbonate may have different particle shapes, such as e.g. the shape of roses, golf balls and/or brains.

According to one embodiment, the surface-reacted calcium carbonate has a specific surface area of from 15 $m^2/g$ to 200 $m^2/g$, preferably from 20 $m^2/g$ to 180 $m^2/g$, and most preferably from 25 $m^2/g$ to 160 $m^2/g$, measured using nitrogen and the BET method. The BET specific surface area in the meaning of the present invention is defined as the surface area of the particles divided by the mass of the particles. As used therein the specific surface area is measured by adsorption using the BET isotherm (ISO 9277: 2010) and is specified in $m^2/g$.

It is a requirement of the present invention that the surface-reacted calcium carbonate has a volume median particle size $d_{50}$ from 0.1 to 90 μm. According to one embodiment the surface-reacted calcium carbonate has a volume median particle size $d_{50}$ from 0.1 to 75 μm, preferably from 0.5 to 50 μm, more preferably from 1 to 40 μm, even more preferably from 1.2 to 30 μm, and most preferably from 1.5 to 15 μm.

It may furthermore be preferred that the surface-reacted calcium carbonate particles have a volume top cut particle size $d_{98}$ of from 2 to 150 preferably from 4 to 100 more preferably 6 to 80 even more preferably from 8 to 60 μm, and most preferably from 8 to 30 μm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$(wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p. 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi-modal, and by taking the specific pore volume intruded by mercury into pores finer than the modal turning point, i.e. finer than the bi-modal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g. 0.004 to 0.16 µm determined by mercury porosimetry measurement.

According to an exemplary embodiment, the surface-reacted calcium carbonate has a volume median particle size $d_{50}$ from 1.5 to 15 µm, preferably from 4 to 6 µm; a specific surface-area of from 30 to 140 $m^2/g$, preferably from 30 to 100 $m^2/g$, measured using nitrogen and the BET method; and an intra-particle intruded specific pore volume from 0.2 to 2.0 $cm^3/g$, preferably from 0.6 to 1.6 $cm^3/g$, calculated from mercury porosimetry measurement.

Due to the intra and interpore structure of the surface-reacted calcium carbonate, it can be a superior agent to deliver previously adsorbed and/or absorbed materials over time relative to common materials having similar specific surface areas. Thus, generally, any agent fitting into the intra- and/or inter particle pores of the surface-reacted calcium carbonate is suitable to be transported by the surface-reacted calcium carbonate according to the invention. For example, active agents such as those selected from the group comprising pharmaceutically active agents, biologically active agents, disinfecting agents, preservatives, flavouring agents, surfactants, oils, fragrances, essential oils, and mixtures thereof can be used. According to one embodiment, at least one active agent is associated with the surface-reacted calcium carbonate.

According to one embodiment of the present invention, the surface-reacted calcium carbonate comprises an water-insoluble, at least partially crystalline calcium salt of an anion of the at least one acid, which is formed on the surface of the natural ground calcium carbonate or precipitated calcium carbonate. According to one embodiment, the water-insoluble, at least partially crystalline salt of an anion of the at least one acid covers the surface of the natural ground calcium carbonate or precipitated calcium carbonate at least partially, preferably completely. Depending on the employed at least one acid, the anion may be sulphate, sulphite, phosphate, citrate, oxalate, acetate, formiate and/or chloride.

For example, the use of phosphoric acid, $H_2PO_4$ or $HPO_4^{2-}$ as the $H_3O^+$ ion donor may lead to the formation of hydroxylapatite. Therefore, in a preferred embodiment, the at least one water-insoluble calcium salt is hydroxylapatite.

According to one embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Preferably, the surface-reacted calcium carbonate may provide a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

According to one embodiment the surface-reacted calcium carbonate comprises:
(i) a specific surface area of from 15 to 200 $m^2/g$ measured using nitrogen and the BET method according to ISO 9277:2010, and
(ii) an intra-particle intruded specific pore volume in the range of from 0.1 to 2.3 $cm^3/g$ calculated from mercury porosimetry measurement.

In one embodiment of the present invention, the surface-reacted calcium carbonate as described herein is provided in the form of granules. "Granules" in the meaning of the present invention are agglomerates of the surface-reacted calcium carbonate and have a particle size of 20 to 300 µm. That is to say, the granules having a particle size of 20 to 300 µm comprise primary particles of the surface-reacted calcium carbonate having a volume median particle size $d_{50}$ from 0.1 to 90 µm.

The Cosmetic and/or Skin Care Composition

The invention refers to the use of surface-reacted calcium carbonate as defined herein in a cosmetic and/or skin care composition as an agent for modifying the biomechanical properties of the skin.

It was surprisingly found by the inventors that the use of surface-reacted calcium carbonate as defined herein in a cosmetic and/or skin care composition leads to a modification of the biomechanical properties of the skin, especially the facial skin.

For example, it was found that the use of surface-reacted calcium carbonate as defined herein in a cosmetic and/or skin care composition leads to an increased skin firmness. Without wishing to be bound by theory, it is believed that the surface-reacted calcium carbonate as defined herein increases the skin firmness due to its capability to mineralize the skin, especially in form of calcium ions. Such mineralization may induce the biosynthesis of collagen fibres, elastins and/or glycosaminoglycans, and therefore a strengthening of the extracellular matrix of the epidermis and/or dermis. A surface-reacted calcium carbonate comprising hydroxylapatite may be especially suitable for inducing the biosynthesis of such biomaterials. The surface-reacted calcium carbonate as defined herein is thus preferably used as anti-wrinkle agent in the cosmetic and/or skin care composition.

In addition to the foregoing advantages, the inventors found that the application of the surface-reacted calcium carbonate on the skin is not, or at least very seldom, accompanied by negative side-effects such as skin irritation. In particular, it was found that the surface-reacted calcium carbonate is less skin irritant than other calcium carbonate materials such as ground calcium carbonate.

Thus, according to one embodiment, the surface-reacted calcium carbonate does not lead to negative side-effects after application on the skin, and preferably does not lead to skin irritation. According to another embodiment, the surface-reacted calcium carbonate leads to less negative side-effects compared to the use of other calcium carbonate-containing materials, and preferably ground calcium carbonate, in cosmetic and/or skin care compositions. According to yet another embodiment, the surface-reacted calcium carbonate leads to less skin irritation compared to the use of other calcium carbonate-containing materials, and preferably ground calcium carbonate, in cosmetic and/or skin care compositions. "Negative side-effects" in the meaning of the present invention are, for example, skin dryness, skin itching, skin irritation or skin inflammation. "Calcium carbonate-containing materials" in the meaning of the present invention are, for example, materials comprising natural ground calcium carbonates or precipitated calcium carbonates.

According to one embodiment of the present invention, the modification of the biomechanical properties of the skin refers to the skin firmness, preferably to an increased skin firmness. The measurement of skin firmness is routinely practiced in cosmetic and/or skin care research, and thus is part of the skilled person's knowledge. For example, skin firmness is measurable by skin suction methods as described above. One suitable device for measuring skin firmness, skin elasticity, and/or skin plasticity is a MPA 580 Cutometer® from Courage & Khazaka. An "increase" of the skin firmness should be understood as referring to a relative increase of the skin firmness of the applicant prior and after the use of a skin care and/or cosmetic composition as described herein.

According to a preferred embodiment, the surface-reacted calcium carbonate modifies the skin firmness, and more preferably increases the skin firmness, and does not lead to negative side-effects, and more preferably does not lead to skin irritation. According to another preferred embodiment, the surface-reacted calcium carbonate modifies the skin firmness, and more preferably increases the skin firmness, and leads to less negative side-effects, and more preferably to less skin irritation compared to the use of other calcium carbonate-containing materials, and more preferably ground calcium carbonate, in cosmetic and/or skin care compositions.

In addition or alternatively, the modification of the biomechanical properties of the skin may also refer to the skin elasticity, and preferably to an increased elasticity, and/or to the skin plasticity, and preferably to a decreased skin plasticity.

Thus, according to one embodiment, the modification of the biomechanical properties of the skin refers to the skin elasticity, and preferably to an increased elasticity, and/or to the skin plasticity, and preferably to a decreased skin plasticity.

According to another embodiment, the modification of the biomechanical properties of the skin refers to the skin firmness, preferably to an increased skin firmness, and the skin elasticity, preferably to an increased skin elasticity.

According to yet another embodiment, the modification of the biomechanical properties of the skin refers to the skin firmness, preferably to an increased skin firmness, and the skin plasticity, preferably to a decreased skin plasticity.

The use for the modification of the biochemical properties of the skin according to the invention is not limited to a specific age and/or sex of an individual. However, the modification of the skin properties as described herein may be more accentuated for applicants of a certain sex and/or age. According to one embodiment, the skin refers to the skin of a female and/or male applicant, preferably a female applicant. According to one embodiment, the skin refers to the skin of an applicant having an age from 1 to 120 years, preferably from 15 to 100 years, more preferably from 25 to 100 years, even more preferably from 35 to 85 years, and most preferably from 40 to 75 years. According to another embodiment, the skin refers to the skin of a female applicant having an age from 1 to 120 years, preferably from 15 to 100 years, more preferably from 25 to 100 years, even more preferably from 35 to 85 years, and most preferably from 40 to 75 years.

The use of a surface-reacted calcium carbonate for modifying the biomechanical properties of the skin is not limited to a certain skin type or a specific part of skin of the human body. Nevertheless, there may be preferred skin areas on the body, that show a specifically strong modification of biomechanical properties. For example, skin areas, which are specifically exposed to the environment such as the skin of the arms, especially the hands, the skin of the legs, especially the feet, the skin of the neck, the skin of the chest, and/or the skin of the face. Thus, according to one embodiment of the present invention, the skin refers to the skin of the arms, especially the hands, the skin of the legs, especially the feet, the skin of the neck, the skin of the chest, and/or the skin of the face, preferably the skin of the face. According to a preferred embodiment, the skin refers to the skin around the eyes. The modification of the biochemical properties of the skin is not dependent on a certain length of the use of the skin care and/or cosmetic composition as described herein, or a certain time period from one application of the composition to another. However, the modification may be more pronounced, if the use expands over a certain time span and/or if the use is repeated more often. According to one embodiment, the cosmetic and/or skin care composition is used for at least 1 day, preferably at least 5 days, more preferably at least 15 days, and most preferably at least 25 days. According to one embodiment, the cosmetic and/or skin care composition is used at least once a day, preferably once to thrice a day, and most preferably once a day. According to one embodiment, the cosmetic and/or skin care composition is used once a day for at least 1 day, preferably at least 5 days, more preferably at least 15 days, and most preferably at least 25 days.

It is appreciated that the amount of the surface-reacted calcium carbonate in the cosmetic and/or skin care composition may vary in a wide range and may be dependent on the cosmetic and/or skin care composition to be prepared and/or the manufacturer's needs and/or legal requirements. For example, in case a skin care and/or cosmetic composition in form of e.g. a paste or an emulsion is prepared, the amount of the surface-reacted calcium carbonate may be below 50 wt.-%, based on the total weight of the cosmetic and/or skin care composition. On the other hand, in case a skin care and/or cosmetic composition in form of e.g. a powder is prepared, the amount of surface-reacted calcium carbonate may be above 50 wt.-%, based on the total weight of the cosmetic and/or skin care composition.

In general, the surface-reacted calcium carbonate can thus be present in the cosmetic and/or skin care composition in an amount from 0.1 to 90 wt.-%, based on the total weight of the cosmetic and/or skin care composition, and preferably from 0.5 to 80 wt.-%.

According to one embodiment of the present invention, the surface-reacted calcium carbonate is present in the cosmetic and/or skin care composition in an amount from 0.1 to 50 wt.-%, based on the total weight of the cosmetic and/or skin care composition, preferably from 0.5 to 20 wt.-%, more preferably from 1 to 10 wt.-%, and most preferably from 3 to 10 wt.-%.

In an alternative embodiment of the present invention, the surface-reacted calcium carbonate is present in the cosmetic and/or skin care composition in an amount from 50 to 90 wt.-%, based on the total weight of the cosmetic and/or skin care composition, and preferably from 60 to 80 wt.-%.

In case the cosmetic and/or skin care composition is prepared in form of a paste or an emulsion, i.e. not in form of a powder, the pH value of the composition may be adjusted to any value suitable for a cosmetic and/or skin care composition. Thus, the cosmetic and/or skin care composition as described herein is not limited to a specific pH value.

The inventors surprisingly found that the pH value of the cosmetic composition comprising the surface-reacted calcium carbonate according to the invention can be adjusted to a pH value of ≤7.5, and can even be adjusted to a pH value from 4.0 to 7.0 without showing a negative impact on the stability of the calcium carbonate particles. Usually cosmetic compositions containing, for example, ground calcium carbonate tend to become unstable when the pH value is adjusted below 7.05, and especially below 7.0, due to the liberation of carbon dioxide from the carbonate in the acidic medium. Thus, the cosmetic and/or skin care composition comprising the surface-reacted calcium carbonate has an improved acid resistance compared to prior art cosmetic products containing, for example, ground calcium carbonate which has not been surface-reacted as described above. This is particularly advantageous since cosmetic and/or skin care products are usually formulated to have a preferred pH value of below 7.5, or of below 7.0 in order to approach or match the natural pH level of the skin. Without wishing to be bound by theory, the inventors speculate that the surface treatment of the calcium carbonate as defined herein leads to a specific surface structure which exhibits an improved acid resistance compared to a calcium carbonate being not surface-reacted.

The cosmetic and/or skin care composition is however not limited to a pH value of ≤7.5, and may also be adjusted to a pH value of ≤8.5.

The cosmetic and/or skin care composition thus preferably has a pH value of ≤8.5, more preferably ≤8.0, even more preferably ≤7.5, still more preferably ≤7.0 and most preferably from 4.0 to 7.0.

The cosmetic and/or skin care composition may further comprise water and/or at least one oil. Thus, according to one embodiment of the present invention, the cosmetic and/or skin care composition further comprises water. According to another embodiment, the cosmetic and/or skin care composition further comprises at least one oil. According to a preferred embodiment, the cosmetic and/or skin care composition further comprises water and at least one oil. An "oil" in the meaning of the present invention is a liquid or solid silicon- and/or hydrocarbon-containing compound.

The water may be selected from tap water, distilled water, deionized water, or mixtures thereof, and preferably is deionized water.

The at least one oil may be selected from any oil which is suitable to be used in cosmetic and/or skin care compositions. Oils which are suitable for use in cosmetic and/or skin care compositions are known to the skilled person and are described in, for example, Regulation EC No 1223/2009 of the European Parliament and of the Council of 30 Nov. 2009, and must not form part of the list of prohibited substances disclosed therein.

According to one embodiment of the present invention, the at least one oil is selected from the group consisting of vegetable oils and esters thereof, alkanecoconutester, plant extracts, animal fats, siloxanes, fatty acids and esters thereof, petrolatum, glycerides and pegylated derivatives thereof, and mixtures thereof.

For example, a suitable vegetable oil may be palm oil, soybean oil, rapeseed oil, sunflower seed oil, peanut oil, cottonseed oil, palm kernel oil, coconut oil, olive oil, jojoba oil, corn oil, jumbü oil, guava oil, grape seed oi, hazelnut oil, linseed oil, rice bran oil, safflower oil, sesame oil, acai palm oil, graviola oil, tucuma oil, brazil oil, carapa oil, buriti oil, passion fruit oil or pracaxi oil.

Suitable plant extracts may be prepared, for example, from *Castanea Sativa, Prunus Dulcis, Juglans Regia L., Olea Europaea, Helichrysum stoechas, Quercus Robur, Glycyrrhiza Glabra, Vitis Vinifera, Crataegus Monogyna Jacq*, or *Pinus Pinaster*.

Suitable animal fats can be obtained, for example, from tallow.

Suitable siloxanes are, for example, dimethicone, cetyl dimethicone, dimethiconol, detearyl methicone, cyclopentasiloxane, cyclomethicone, stearyl dimethicone, trimethylsilylamodimethicone, stearoxy dimethicone, amodimethicone, behenoxy dimethicone, dimethicone copolyol, polysiloxane, laurylmethicone copolyol or cetyl dimethicone copolyol.

Suitable fatty acids are, for example, palmitic acid, stearic acid, myristic acid, oleic acid, palmitoleic acid, linoleic acid, linolenic acid, capric acid, caprylic acid, arachidonic acid and esters thereof.

Suitable petrolatum may be any petrolatum with a refined grade approved for cosmetic use, and preferably has a melting point between 35° C. and 70° C.

Suitable glycerides are, for example, mono-, di, or triglycerides from palmitic acid, stearic acid, myristic acid, oleic acid, palmitoleic acid, linoleic acid, linolenic acid, capric acid, caprylic acid, and mixtures thereof.

In one embodiment, the at least one oil comprises, preferably consists of, one oil. Alternatively, the at least one oil comprises, preferably consists of, two or more oils. For example, the at least one oil comprises, preferably consists of, two or three oils. Preferably, the at least one oil comprises, preferably consists of, two or more oils.

It is appreciated that the cosmetic and/or skin care composition may comprise the water and/or the at least one oil and their amounts in dependence of the cosmetic and/or skin care composition to be prepared and/or the manufacturer's needs. According to one embodiment, the water is present in an amount of from 1 to 95 wt.-%, preferably from 15 to 90 wt.-%, more preferably from 25 to 80 wt.-%, even more preferably from 35 to 75 wt.-%, and most preferably from 45 to 65 wt.-%, based on the total weight of the cosmetic and/or skin care composition. According to another embodiment, the at least one oil is present in an amount of from 1 to 95 wt.-%, preferably from 2 to 75 wt.-%, more preferably from 5 to 55 wt.-%, even more preferably from 7.5 to 35 wt.-%, and most preferably from 10 to 20 wt.-%, based on the total weight of the cosmetic and/or skin care composition.

In case the cosmetic and/or skin care composition comprises water and at least one oil, the composition may be a water-based dispersion or an oil-based dispersion. Thus, according to one embodiment, the cosmetic and/or skin care composition is a water-based dispersion. According to another embodiment, the composition is an oil-based dispersion. According to a preferred embodiment, the cosmetic and/or skin care composition is a water-based dispersion. A "water-based dispersion" in the meaning of the present invention refers to a composition wherein water forms a continuous phase and the oil a dispersed phase, i.e. the oil is dispersed in the continuous water phase. An "oil-based dispersion" in the meaning of the present invention refers to a composition wherein oil forms a continuous phase and water a dispersed phase, i.e. water is dispersed in the continuous water phase. According to yet another embodiment, the water is present in an amount of from 1 to 95 wt.-%, preferably from 15 to 90 wt.-%, more preferably from 25 to 80 wt.-%, even more preferably from 35 to 75 wt.-%, and most preferably from 45 to 65 wt.-%, and the at least one oil is present in an amount of from 1 to 95 wt.-%, preferably from 2 to 75 wt.-%, more preferably from 5 to 55 wt.-%, even more preferably from 7.5 to 35 wt.-%, and most preferably from 10 to 20 wt.-%, based on the total weight of the cosmetic and/or skin care composition.

As described above, the intra and interpore structure of the surface-reacted calcium carbonate can make it a superior agent to deliver previously adsorbed and/or absorbed materials over time relative to common materials having similar specific surface areas. Thus, generally, any agent fitting into the intra- and/or inter particle pores of the surface-reacted calcium carbonate is suitable to be transported by the surface-reacted calcium carbonate according to the invention. Accordingly, it is possible that the cosmetic and/or skin care composition comprises at least one active agent being adsorbed onto and/or absorbed into the surface of the surface-reacted calcium carbonate. According to one embodiment of the present invention, the cosmetic and/or skin care composition comprises at least one active agent being adsorbed onto and/or absorbed into the surface of the surface-reacted calcium carbonate.

According to a preferred embodiment of the present invention, the at least one active agent is selected from pharmaceutically active agents, biologically active agents, vitamins, disinfecting agents, preservatives, flavouring agents, surfactants, oils, fragrances, essential oils such as limonene or mint oil, and mixtures thereof, and preferably biologically active agents, scented oils and essential oils.

The at least one active agent may be adsorbed onto and/or absorbed into the surface of the surface-reacted calcium carbonate in specific amounts. According to one embodiment of the present invention, the amount of the at least one agent being adsorbed onto and/or absorbed into the surface of the surface-reacted calcium carbonate ranges from 0.1 to 99 wt.-%, based on the weight of the surface-reacted calcium carbonate, preferably ranges from 30 to 95 wt.-%, more preferably from 50 to 90 wt.-%, and most preferably from 70 to 85 wt.-%.

The cosmetic and/or skin care composition may also comprise further additives. Additives that are suitable for cosmetic compositions are known to the skilled person and are described in, for example, Regulation EC No 1223/2009 of the European Parliament and of the Council of 30 Nov. 2009, and must not form part of the list of prohibited substances disclosed therein. According to one embodiment of the present invention, the cosmetic and/or skin care composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

For example, the emulsifier can be an ionic emulsifier, more preferably and anionic or cationic emulsifier. The emulsifier can be of natural vegetable origin e.g. polyglycerol ester or synthetic. More preferably, the emulsifier may be selected from the group comprising PEG compounds, PEG-free emulsifier, silicone-based emulsifier, silicones, waxes and mixtures thereof. For example, the emulsifier may be selected from the group comprising PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, carbomer, carboxymethylcellulose, ceresin (aka mineral wax), diethanolamine (DEA), isopropyl stearate, isopropyl laurate, isopropyl palmitate, isopropyl oleate, polysorbate 20, polysorbate 60, polysorbate 80, propylene glycol, sorbitan stearate, sorbitan laurate, sorbitan palmitate, sorbitan oleate, steareth-20, triethanolamine (TEA), beeswax, candelilla wax, carnauba wax, cetearyl alcohol, cetearyl wheat bran glycosides, cetearyl wheat straw glycosides, decyl glucoside, jojoba, lecithin, vegetable glycerin, xanthan gum, coco glucoside, coconut alcohol, arachidyl alcohol, behenyl alcohol, arachidyl glucoside, and mixtures thereof.

The fragrance may be selected from a natural and/or synthetic fragrance known as being suitable in cosmetic formulations.

The colorant may be selected from a natural and/or synthetic colorant, pigment or dye such as $Fe_2O_3$, ZnO, $TiO_2$, mica, talc, bismuth oxychloride, and mixtures thereof.

According to one embodiment, the skin tanning compound is preferably dihydroxyacetone (DHA) and/or erythrulose. For example, the skin tanning compound may be dihydroxyacetone (DHA) or erythrulose. Alternatively, the skin tanning compound may be dihydroxyacetone (DHA) in combination with erythrulose.

According to one embodiment, the cosmetic and/or skin care composition further comprises at least one emollient. Examples of suitable emollients are isocetylstearoylstearate, ethylhexyl stearate, octyldodecyl stearoyl stearate, isocetyl stearate, isopropyl isostearate, isostearyl isostearate, ethylhexyl hydroxystearate, ethylhexyl palmitate, isopropyl palmitate, neopentyl glycol diheptanoate, ethylhexyl isononanoate, isononyl isononanoate, cetearyl isononanoate, cetearyl octanoate, diisopropyl adipate, dicapryl adipate, diisostearylmalate, decyl oleate, isodecyl oleate, diisopropyl myristate, isostearyl neopentanoate, octyl dodecyl neopentanoate, ethylhexyl cocoate, PEG-7 glyceril cocoate, C12-15 alkyl benzoate, C16-17 alkyl benzoate, stearyl benzoate, isostearyl benzoate, ethylhexyl benzoate, octyldodecyl benzoate, cocoglyceride, coconut alkanes, coco-caprylate/caprate, and mixtures thereof. For example, the cosmetic composition may further comprise a mixture of cocoglyceride, isononyl isononanoate, coconut alkanes and coco-caprylate/caprate as emollient.

Additionally or alternatively, the cosmetic and/or skin care composition further comprises at least one thickener. Examples of suitable thickener for a water-based dispersion are thickener based on silicate such as magnesium silicate, aluminium silicate and mixtures thereof, hydroxyethylcellulose, cellulose, microcrystalline cellulose, xanthan gum or polyacrylamide. Examples of suitable thickener for an oil-based dispersion are selected from the group comprising silicate such as magnesium silicate, aluminium silicate, silica dimethylsilicate, hydrophobic fumed silica, polyacrylic acid, salts of polyacrylic acid, derivatives of polyacrylic acid, PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, methyl cellulose, ethyl cellulose, propyl cellulose, carboxymethylcellulose, xanthan gum, ammonium acryloyldimethyltaurate/VP copolymer and mixtures thereof.

Additionally or alternatively, the cosmetic and/or skin care composition further comprises at least one preserving agent. Examples of suitable preserving agents are phenoxyethanol, ethylhexylglycerin, parabens such as methyl paraben, ethyl paraben, propyl paraben, butyl paraben, isobutyl paraben and mixtures thereof, benzoic acid, sodium benzoate, sorbic acid, potassium sorbate and mixtures thereof, or plant extracts with preservative function such as rosemary extracts. For example, said mixture may comprise phenoxyethanol, methyl paraben, ethyl paraben and isobutyl paraben.

Examples of suitable chelating agents are a polyphosphate, ethylenediamine-N,N,N',N'-tetraacetic acid (EDTA), pyridine-2,6-dicarboxylic acid (DPA), diethylenetriaminepentaacetic acid (DTPA), N,N-bis(carboxymethyl)glycine (NTA), ammonium diethyldithiophosphate (DDPA), disodium ethylenediamine-tetraacetate ($Na_2H_2EDTA$), calcium-disodium-ethylenediamine-tetraacetate ($CaNa_2EDTA$), citric acid and salts of citric acid, sodium gluconate, and mixtures thereof.

Examples of suitable wetting agents are primary alcohols such as 1-ethanol, 1-propanol, 1-butanol, isobutanol 1-pentanol, isoamyl alcohol, 2-methyl-1butanol, 1-hexanol, 1-heptanol, 1-octanol, 1-nonanol, 1-decanol, 1-undecanol, 1-dodecanol, 1-tridecanol, 1-tetradecanol, 1-pentadecanol, cetyl alcohol, 1-heptadecanol, stearyl alcohol, 1-nonadecanol and mixtures thereof, secondary alcohols such as isopropanol, 2-butanol, 2-pentanol, 2-hexanol, 2-heptanol and mixtures thereof, tertiary alcohols such as tert.-butyl alcohol, tert.-amyl alcohol, 2-methyl-2-pentanol, 2-methylhexan-2-ol, 2-methylheptan-2-ol, 3-methyl-3-pentanol, 3-methyloctan-3-ol and mixtures thereof, diols such as 1,2-diols or 1,3-diols, e.g. 1,3-propandiol, urea, and mixtures thereof.

Examples of suitable antioxidants are butylhydroxyanisol (BHA), butylhydroxytoluol (BHT), gallate, carotinoid, polyphenols such as resveratrol, flavonoid and mixtures thereof, derivatives of polyphenols, ascorbic acid and salts thereof, tocopherol and salts thereof, betacarotin, ubichinon, tocotrienol, dihydroquercetin, antioxidants of natural origin, and mixtures thereof.

Examples of suitable pigments are inorganic red pigments such as iron oxide, ferric hydroxide and iron titanate, inorganic brown pigments such as γ-iron oxide, inorganic yellow pigments such as yellow iron oxide and yellow ocher, inorganic black pigments such as black iron oxide and carbon black, inorganic purple pigments such as manganese violet and cobalt violet, inorganic green pigments such as chromium hydroxide, chrome oxide, cobalt oxide and cobalt titanate, inorganic blue pigments such as iron blue and ultramarine, particulate powders such as particulate titanium oxide, particulate cerium oxide and particulate zinc oxide, laked tar dyes, laked natural dyes, and synthetic resin powders combining foregoing powders.

The bleaching agent may be selected from one or more of a vitamin B3 compound or its derivative e.g. niacin, nicotinic acid or niacinamide or other well-known bleaching agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), moms alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred bleaching agents, most preferred being niacinamide. Niacinamide, when used, is preferably present in an amount in the range of 0.1 to 10 wt.-%, more preferably 0.2 to 5 wt.-%, based on the total weight of the cosmetic composition.

The minerals may be selected from any minerals suitable for the use in a cosmetic and/or skin care composition. For example, the cosmetic and/or skin care composition may contain silicates such as talc, mica and/or kaolin. UV-A and/or UV-B filter may be selected from inorganic UV filter and/or organic UV filter. Suitable inorganic UV filter are, for example, selected from the group consisting of titanium dioxide, zinc oxide, iron oxide, hydroxyapatite, cerium oxide, calcium-doped cerium oxide, cerium phosphate, and mixtures thereof. Suitable organic UV filter are, for example, selected from the group comprising cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof.

It is appreciated that the cosmetic composition may comprise the at least one further additive and its amount in dependence of the cosmetic composition to be prepared and/or the manufacturer's needs. For example, the cosmetic composition may comprise 0.1 to 10 wt.-% of thickeners, stabilizers, chelating agents, bleaching agents, wetting agents, emulsifiers, emollients, and/or skin tanning compounds, and/or 0.1 to 15 wt.-% of preserving agents, fragrances, colorants, antioxidants, minerals, pigments, UV-A and/or UV-B filter wherein the wt.-% is based on the total weight of the cosmetic composition.

In one embodiment, the at least one additive comprises, preferably consists of, one additive. Alternatively, the at least one additive comprises, preferably consists of, two or more additives. For example, the at least one additive comprises, preferably consists of, ten to fifteen additives. Preferably, the at least one additive comprises, preferably consists of, two or more additives.

The cosmetic and/or skin care composition may be provided in the form of any cosmetic and/or skin care product being applicable to the skin of the face and/or body. According to one embodiment of the present invention, the cosmetic and/or skin care composition is selected from an eye make-up product, a facial make-up product, a lip care product, a hand care product, a skin care product, or a combination product thereof.

Furthermore, the cosmetic and/or skin care composition may have a certain Brookfield viscosity. For the purpose of the present invention, the term "viscosity" or "Brookfield viscosity" refers to Brookfield viscosity. The Brookfield viscosity is for this purpose measured by a Brookfield (Typ RVT) viscometer at 25° C.±1° C. at 100 rpm after 30 seconds using an appropriate spindle and is specified in mPa·s. According to one embodiment of the present invention, the cosmetic and/or skin care composition has a Brookfield viscosity in a range from 4 000 to 50 000, preferably from 10 000 to 45 000, more preferably from 15 000 to 40 000, even more preferably from 20 000 to 40 000, and most preferably from 25 000 to 40 000 mPa·s at 25° C.

Preparation of the Cosmetic and/or Skin Care Composition

The method for the preparation of the cosmetic and/or skin care composition comprises at least the provision of a surface-reacted calcium carbonate as an agent for modifying the biomechanical properties of the skin. The surface-reacted calcium carbonate has a volume median particle size $d_{50}$ from 0.1 to 90 µm and is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

The surface-reacted calcium carbonate may be provided in any suitable liquid or dry form. For example, the surface-reacted calcium carbonate may be in form of a powder and/or a suspension. The suspension can be obtained by mixing the surface-reacted calcium carbonate with a solvent, preferably water. The surface-reacted calcium carbonate to be mixed with a solvent, and preferably water, may be provided in any form, for example, as suspension, slurry, dispersion, paste, powder, a moist filter cake or in pressed or granulated form, and preferably is provided as a powder.

The term "dispersion" or "suspension" in the meaning of the present invention refers to a system comprising a dispersing medium or solvent and at least one inorganic particulate material, wherein at least a part of the particles of the at least one inorganic particulate material are present as insoluble solids or suspended particles in the dispersing medium or solvent.

The suspension can be undispersed or dispersed, i.e. the suspension includes a dispersant, and thus, forms a dispersion, e.g. an aqueous dispersion. Suitable dispersants are known in the art, and may be selected, e.g., from polyelectrolytes, polyhydroxystearic acid, acetylacetone, propylamine, oleic acid, polyacrylates, carboxymethylcellulose based dispersants, and mixtures thereof.

The solids content of the suspension, preferably aqueous suspension, of the surface-reacted calcium carbonate may be from 1 to 85 wt.-%, more preferably from 5 to 75 wt.-%, and most preferably from 10 to 40 wt.-%, based on the total weight of the suspension.

In case the surface-reacted calcium carbonate is provided in dry form, the moisture content of the surface-reacted calcium carbonate can be between 0.01 and 5 wt.-%, based on the total weight of the surface-reacted calcium carbonate. The moisture content of the surface-reacted calcium carbonate can be, for example, less than or equal to 1.0 wt.-%, based on the total weight of the surface-reacted calcium carbonate, preferably less than or equal to 0.5 wt.-%, and more preferably less than or equal to 0.2 wt.-%. According to another example, the moisture content of the surface-reacted calcium carbonate may be between 0.01 and 0.15 wt.-%, preferably between 0.02 and 0.10 wt.-%, and more preferably between 0.03 and 0.07 wt.-%, based on the total weight of the surface-reacted calcium carbonate.

The method for the preparation of the cosmetic and/or skin care composition may further comprise the provision of water and/or at least one oil and the mixing of the water and/or at least one oil with the surface-reacted calcium carbonate.

The mixing of the water and/or the at least one oil and the surface-reacted calcium carbonate may be carried out in any manner known by the skilled person. The mixing may be carried out under conventional mixing conditions. The skilled man will adapt these mixing conditions (such as the configuration of mixing pallets and mixing speed) according to his process equipment. It is appreciated that any mixing method which would be suitable to form a cosmetic and/or skin care composition may be used.

In case, the method further comprises the provision of water and at least one oil, the mixing may be carried out in any order. Preferably, the water and the at least one oil are combined and mixed to form a mixture followed by the addition and mixing of the surface-reacted calcium carbonate.

Mixing can be carried out at temperatures typically used for preparing a cosmetic base formulation. Preferably, mixing is carried out at a temperature in the range from 15 to 100° C., more preferably from 20 to 85° C. such as of about 45° C.

The method for the preparation of the cosmetic and/or skin care composition may further comprise the provision of at least one additive. The combining and mixing of the at least one additive and the surface-reacted calcium carbonate may also be carried out under conventional mixing conditions. The skilled man will adapt these mixing conditions (such as the configuration of mixing pallets and mixing speed) according to his process equipment. It is appreciated that any mixing method which would be suitable to form a cosmetic and/or skin care composition may be used.

In case, the method comprises the provision of the surface-reacted calcium carbonate, water and/or at least one oil, and at least one additive, and preferably two or more additives, the combining and mixing may be carried out in any order.

For example, the method for the preparation of the cosmetic and/or skin care composition may comprise the steps of:
a) providing a surface-reacted calcium carbonate as described herein,
b) providing water,
c) providing at least one oil,
d) providing two or more additives,
e) combining and mixing one or more of the two or more additives with water to form a first mixture,
f) combining and mixing one or more of the two or more additives with the at least one oil to form a second mixture
g) combining and mixing the first and the second mixture to form a third mixture,
h) optionally combining and mixing the third mixture with one or more of the two or more additives, to form a fourth mixture,
i) combining and mixing the surface-reacted calcium carbonate with the third mixture of step g) or the fourth mixture of step h).

The scope and interest of the invention will be better understood based on the following examples which are intended to illustrate certain embodiments of the present invention and are non-limitative.

EXAMPLES

1. Measurement Methods

In the following, measurement methods implemented in the examples are described.

Particle Size Distribution

Volume determined median particle size $d_{50}$(vol) and the volume determined top cut particle size $d_{98}$(vol) was evaluated using a Malvern Mastersizer 2000 Laser Diffraction System (Malvern Instruments Plc., Great Britain). The $d_{50}$(vol) or $d_{98}$(vol) value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments.

The weight determined median particle size $d_{50}$(wt) was measured by the sedimentation method, which is an analysis of sedimentation behaviour in a gravimetric field. The measurement was made with a Sedigraph™ 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Specific Surface Area (SSA)

The specific surface area was measured via the BET method according to ISO 9277 using nitrogen, following conditioning of the sample by heating at 250° C. for a period of 30 minutes. Prior to such measurements, the sample was filtered within a Buchner funnel, rinsed with deionised water and dried overnight at 90 to 100° C. in an oven. Subsequently, the dry cake was ground thoroughly in a mortar and the resulting powder was placed in a moisture balance at 130° C. until a constant weight was reached.

Intra-Particle Intruded Specific Pore Volume (in $Cm^3/g$)

The specific pore volume was measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step was 20 seconds. The sample material was sealed in a 5 $cm^3$ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

2. Pigment Materials
GCC1
GCC 1 is high purity natural calcium carbonate obtained from limestone, sold by Omya, and shows the characteristics listed in Table 1 below.
SRCC 1
SRCC 1 has a $d_{50}$=1.6 µm, $d_{98}$=10.0 µm, a SSA=31.4 $m^2/g$ and an intra-particle intruded specific pore volume of 0.837 $cm^3/g$ (for the pore diameter range of 0.004 to 0.59 µm).

SRCC 1 was obtained by preparing 7 liters of an aqueous suspension of ground calcium carbonate in a mixing vessel by adjusting the solids content of a ground marble calcium carbonate from Omya Madencilik A. S., Turkey, having a mass based median particle size of 0.4 µm, as determined by sedimentation, such that a solids content of 15 wt.-%, based on the total weight of the aqueous suspension, is obtained.

Whilst mixing the slurry, 290 g phosphoric acid was added in form of an aqueous solution containing 10 wt.-% phosphoric acid to said suspension over a period of 100 minutes at a temperature of 70° C. After the addition of the acid, the slurry was stirred for additional 5 minutes, before removing it from the vessel, filtering the product for removing excess water and then further drying in an oven.

TABLE 1

Properties of used pigment materials

| Products | $d_{50}$ (µm) | $d_{98}$ (µm) | SSA ($m^2/g$) | Oil Absorption (g/100 g) | R(y) (%) |
|---|---|---|---|---|---|
| SRCC 1 | 1.6 | 10.0 | 31.4 | 44 | 96.4 |
| GCC 1 | 0.85 | 5.0 | 9.7 | 18 | 91.7 |

3. Other Materials—Tradenames/Suppliers/INCI Names of Ingredients

TABLE 2

Ingredients for a cosmetic and/or skin care composition

| | Ingredients | INCI Nomenclature | Suppliers |
|---|---|---|---|
| A) | Lanette O | Cetearyl Alcohol | 8) |
| | Imwitor 372P | Glyceryl Stearate Citrate | 1) |
| | Almond Oil | *Prunus Amygdalus Dulcis* (Sweet Almond) Oil | 3) |
| | Apricot Oil | *Prunus Armeniaca* (Apricot) Kernel Oil | 3) |
| | KCC SF1000N-100 cSt | Polydimethylsiloxane | 2) |
| | KCC 4130P | Stearyl Dimethicone | 2) |
| | Coconut Oil | *Cocos nucifera* Oil | 7) |
| B) | Water dem. | Aqua (water) | |
| | 1,2-Propanediol | Propylene Glycol | |
| | Glycerin | Glycerin | |
| | Xanthan Gum | Xanthan Gum | 5) |
| | Potassium Sorbate | Potassium Sorbate | 8) |
| | Sodium Chloride | Sodium Chloride | |
| D) | Phenochem NIB | Methylparaben (and) Ethylparaben (and) Butylparaben (and) Propylparaben (and) Phenoxyethanol | 6) |

1) Sasol GmbH, Germany
2) KCC Silicone Corporation, Korea
3) Hänseler AG, Switzerland
4) Sigma Aldrich, Switzerland
5) Omya Hamburg GmbH, Germany
6) SLI Chemicals GmbH, Germany
7) Georges Walther AG, Switzerland
8) Cognis GmbH, Germany 4. Biomechanical Properties—Test Results

TABLE 3

Skin care and/or cosmetic compositions

| | | | Composition No. | |
|---|---|---|---|---|
| | | | 1 | 2 |
| | Ingredients | INCI Nomenclature | % w/w | % w/w |
| A) | Lanette O | Cetearyl Alcohol | 2.00 | 2.00 |
| | Imwitor 372P | Glyceryl Stearate Citrate | 5.00 | 5.00 |
| | Almond Oil | *Prunus Amygdalus Dulcis* (Sweet Almond) Oil | 2.00 | 2.00 |
| | Apricot Oil | *Prunus Armeniaca* (Apricot) Kernel Oil | 3.00 | 3.00 |
| | KCC SF1000N-100 cSt | Polydimethylsiloxane | 2.00 | 2.00 |
| | KCC 4130P | Stearyl Dimethicone | 2.00 | 2.00 |
| | Coconut Oil | *Cocos nucifera* Oil | 3.00 | 3.00 |
| B) | Water dem. | Aqua (water) | add. 100 | add. 100 |
| | 1,2-Propanediol | Propylene Glycol | 4.00 | 4.00 |
| | Glycerin | Glycerin | 3.00 | 3.00 |
| | Xanthan Gum | Xanthan Gum | 0.20 | 0.20 |
| | Potassium Sorbate | Potassium Sorbate | 0.20 | 0.20 |
| | Sodium Chloride | Sodium Chloride | 0.90 | 0.80 |
| C) | GCC1 | | 5 | |
| | SRCC1 | | | 5 |
| D) | Phenochem NIB | Methylparaben (and) Ethylparaben (and) Butylparaben (and) Propylparaben (and) Phenoxyethanol | 1.00 | 1.00 |
| | | | 100.00 | 100.00 |

The cosmetic compositions were prepared as follows:
Heat phase A & B separately at 80° C.
Add phase B to phase A while stirring (Heidolph, Faust, 300 rpm)
Cool down at room temperature
Add part C & D and homogenize (Ultra Turrax T25-D, IKA, 24 000 rpm)
Adjust the pH at 6.0 using lactic acid (10%-solution)

4.1 Measurement of Biomechanical Properties of the Skin

Firmness measurements were carried out with a MPA 580 Cutometer® (Courage & Khazaka). The measurement is based on an in vivo non-invasive method to evaluate skin rheological properties: measures of biological extensibility and elasticity variations. The technique consists on the suction of the skin in the orifice of a probe by a constant vacuum pressure and for a constant duration. The depth of penetration of the skin into the probe is measured, without friction and mechanical effects, by using two optical prisms located at the opening of this probe. Cutaneous skin elasticity was performed with a 2 mm probe with a 450 mbar constant pressure and one cycle of measurement. Suction and relaxation times are 3 seconds each. Each measurement is an average of two acquisitions. The cutaneous firmness parameter Uf was studied. FIG. 1 shows a skin deformation curve obtained with a Cutometer® and the measured parameters.

Table 4 shows test results for a comparative skin care and/or cosmetic composition comprising GCC 1.

TABLE 4

Comparative skin care and/or cosmetic composition comprising GCC 1

| Parameters | Kinetic | ΔΔ Dx-DO (mean ± SEM) | % of efficacy | % of subjects with an improvement |
|---|---|---|---|---|
| Firmness | R0 (Uf) | Δ D28 | −0.083 ± 0.014 | +22% | 90 |

It can be gathered from the data shown in Table 4 that after 28 days of once daily use, the composition comprising GCC 1 induced a certain improvement of biomechanical properties of the skin, characterized by: a decrease in firmness parameter (R0 (Uf)) of 22% on average.

TABLE 5

Inventive skin care and/or cosmetic composition comprising SRCC 1

| Parameters | Kinetic | ΔΔ Dx-DO (mean ± SEM) | % of efficacy | % of subjects with an improvement |
|---|---|---|---|---|
| Firmness | R0 (Uf) | Δ D28 | −0.103 ± 0.020 | +27% | 90 |

It can be gathered from the data shown in Table 5 that after 28 days of once daily use, the composition comprising SRCC 1 induces an improvement of biomechanical properties of the skin. The improved is characterized by a significant decrease in firmness parameter (R0 (Uf)) of 27% on average, and thus in an increased skin firmness. Furthermore, a firm skin was observed in 90% of the subjects.

By comparing the data shown in Table 4 and Table 5, it can be seen that the inventive composition comprising a surface-reacted calcium carbonate provides better results for the modification of skin firmness when compared to a composition comprising a ground calcium carbonate.

4.2 Sensory Evaluation of the Skin Care and/or Cosmetic Composition

Composition 1 comprising GCC 1 and composition 2 comprising SRCC 1 were tested by subjects concerning unpleasant skin sensations such as skin irritation. The results of the study were evaluated after a time period of 28 days.

During the test study with composition 1 comprising GCC 1, 5% of the subjects reported cutaneous/ocular irritation sensations.

During the test study, none of the subjects complained about irritation sensations after or during the application of composition 2 comprising SRCC1.

Thus, the cosmetic and/or skin care composition comprising SRCC 1 is not irritant, and therefore in any case, less irritant to the skin than the cosmetic and/or skin care composition comprising GCC 1.

The invention claimed is:

1. A method for modifying the biomechanical properties of the skin comprising applying to the skin a cosmetic and/or skin care composition comprising a surface-reacted calcium carbonate, wherein
the surface-reacted calcium carbonate has a volume median particle size $d_{50}$ from 0.1 to 90 μm,
the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
the amount of the surface-reacted calcium carbonate in the cosmetic and/or skin care composition is from 0.1 to 5 wt-% based on the total weight of the cosmetic and/or skin care composition, and
the method results in a modification of one or more of firmness of the skin, elasticity of the skin, or plasticity of the skin.

2. The method of claim 1, wherein the surface-reacted calcium carbonate has a volume median particle size $d_{50}$ from 0.5 to 50 μm.

3. The method of claim 1, wherein the surface-reacted calcium carbonate has a specific surface area of from 15 $m^2/g$ to 200 $m^2/g$, measured using nitrogen and the BET method.

4. The method according to claim 1, wherein
the natural ground calcium carbonate is selected from the group consisting of marble, chalk, limestone, and mixtures thereof, or
the precipitated calcium carbonate is selected from the group consisting of precipitated calcium carbonates having an aragonitic, vateritic or calcitic crystal form, and mixtures thereof.

5. The method according to claim 1, wherein the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof.

6. The method according to claim 1, wherein the modification of the biomechanical properties of the skin refers to the skin firmness.

7. The method according to claim 1, wherein the skin refers to the skin of the arms, the skin of the hands, the skin of the legs, the skin of the feet, the skin of the neck, the skin of the chest, and/or the skin of the face.

8. The method according to claim 1, wherein the cosmetic and/or skin care composition has a pH value of ≤8.5.

9. The method according to claim 1, wherein the surface-reacted calcium carbonate is present in the cosmetic and/or skin care composition in an amount from 0.1 to 50 wt.-%, based on the total weight of the composition.

10. The method according to claim 1, wherein the cosmetic and/or skin care composition further comprises water and/or at least one oil.

11. The method according to claim 1, wherein the cosmetic and/or skin care composition comprises at least one active agent being adsorbed onto and/or absorbed into the surface of the surface-reacted calcium carbonate.

12. The method according to claim 11, wherein the at least one active agent is selected from pharmaceutically active agents, biologically active agents, vitamins, disinfecting agents, preservatives, flavouring agents, surfactants, oils, fragrances, essential oils, and mixtures thereof.

13. The method according to claim 1, wherein the composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

14. The method according to claim 1, wherein the cosmetic and/or skin care composition is selected from an eye make-up product, a facial make-up product, a lip care product, a hand care product, a skin care product, or a combination product thereof.

15. The method according to claim 1, wherein the surface-reacted calcium carbonate does not lead to negative side-effects or does not lead to skin irritation, after application on the skin.

16. The method according to claim 1, wherein the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof.

17. The method according to claim 1, wherein the modification of the biomechanical properties of the skin refers to an increased skin firmness.

18. The method according to claim 1, wherein the skin refers to the skin of the face.

19. The method according to claim 1, wherein the cosmetic and/or skin care composition has a pH value of ≤8.0.

20. The method according to claim 1, wherein the surface-reacted calcium carbonate is present in the cosmetic and/or skin care composition in an amount from 0.5 to 20 wt.-%, based on the total weight of the composition.

21. The method according to claim 1, wherein the cosmetic and/or skin care composition further comprises water, and/or at least one oil selected from the group consisting of vegetable oils and esters thereof, alkanecoconutester, plant extracts, animal fats, siloxanes, silicones, fatty acids and esters thereof, petrolatum, glycerides and pegylated derivatives thereof.

* * * * *